(12) United States Patent
Ostergard

(10) Patent No.: US 11,351,051 B1
(45) Date of Patent: Jun. 7, 2022

(54) ANKLE BRACE

(71) Applicant: Doak Ostergard, Lincoln, NE (US)

(72) Inventor: Doak Ostergard, Lincoln, NE (US)

( * ) Notice: Subject to any disclaimer, the term of this patent is extended or adjusted under 35 U.S.C. 154(b) by 365 days.

(21) Appl. No.: 16/406,489

(22) Filed: May 8, 2019

(51) Int. Cl.
*A61F 5/01* (2006.01)
*A43B 7/20* (2006.01)

(52) U.S. Cl.
CPC ............. *A61F 5/0111* (2013.01); *A43B 7/20* (2013.01)

(58) Field of Classification Search
CPC .... A61F 5/0102; A61F 5/0111; A61F 5/0195; A61F 5/0127; A61F 5/0585; A61F 5/0113; A61F 2002/6614; A61F 2002/7862; A61F 5/0109; A61F 5/022; A61F 13/066; A61F 13/064; A61F 2/6607; A61F 5/01; A61F 5/00; A43B 3/0005; A43B 7/20; A43B 5/1691; A43B 21/32

See application file for complete search history.

*Primary Examiner* — Ophelia A Hawthorne
(74) *Attorney, Agent, or Firm* — Dennis L. Thomte; Thomte Patent Law Office LLC

(57) ABSTRACT

An ankle brace which is positioned on an ankle and shoe of a person which incorporates a tensioning structure which permits full range of motion to the ankle joint but which prevents the ankle joint from moving past its normal range of motion to protect the ankle joint. The ankle brace is configured to permit a person wearing the brace to position the same on a shoe.

5 Claims, 9 Drawing Sheets

ANKLE BRACE

BACKGROUND OF THE INVENTION

Field of the Invention

This invention relates to an ankle brace and more particularly to an ankle brace including a tension system which functionally stabilizes the ankle as it reaches extreme ranges of motion.

Description of the Related Art

Conventional braces for protecting joints of the body do so by restricting or limiting motion of the joint to which it is applied to prevent a new injury or to protect a pre-existing injury. An ankle joint, just like all the joints in the human body, has a natural range of motion that it can move through without causing damage to itself. As it reaches the end of these ranges, the body has structure such as ligaments and tendons to create tension to end range of motion and protect the joint. Many of the prior art ankle braces do prevent the ankle from exceeding its extreme ranges of motion but do not provide the necessary flexibility to permit the athlete to function normally.

Applicant's ankle braces described and shown in Applicant's earlier patents and patent applications represented improvements in the ankle brace art. The instant invention represents a further improvement in the ankle brace art.

SUMMARY OF THE INVENTION

This Summary is provided to introduce a selection of concepts in a simplified form that are further described below in the Detailed Description. This Summary is not intended to identify key aspects or essential aspects of the claimed subject matter. Moreover, this Summary is not intended for use as an aid in determining the scope of the claimed subject matter.

An ankle brace is disclosed for use with an athletic shoe or a non-athletic shoe having a lateral side, a medial side, an upper part with an upper end, a lacing closure, with upper and lower ends, including a plurality of spaced-apart pairs of eyelets adapted to have a shoelace threaded therein. The brace is configured to be positioned over and under the shoe. The brace of this invention includes a lower body having a flexible lateral portion having an upper end, a lower end, a forward end, a rearward end, an outer side and an inner side. The lateral portion of the lower body includes an inclined portion, having upper and lower ends, extending upwardly and forwardly from the forward end thereof. The inclined portion of the lateral portion of the lower body has at least first and second openings and preferably a third opening formed therein at the upper end thereof. The lower body of the brace also includes a flexible medial portion having an upper end, a lower end, a rearward end, an outer side and an inner side. The medial portion of the lower body has an inclined portion, having upper and lower ends, extending upwardly and forwardly from the forward end thereof. The inclined portion of the medial portion of the lower body has at least first and second openings and preferably a third opening formed therein at the upper end thereof. The rearward ends of the lateral and medial portions of the lower body are joined together. The lower ends of the lateral and medial portions are joined together so as to pass beneath the shoe.

The brace also includes an U-shaped upper cuff having a lateral portion and a medial portion with the lateral portion of the upper cuff having a forward end, a rearward end, an upper end and a lower end and with the medial portion of the upper cuff having a forward end, a rearward end, an upper end and a lower end. A first D-ring is secured to the outer side of the lateral portion of the upper cuff at the forward end thereof. A second D-ring is also secured to the outer side of the lateral portion of the upper cuff below the first D-ring. A third D-ring is secured to the outer side of the medial portion of the upper cuff at the forward end thereof. A fourth D-ring is secured to the outer side of the medial portion of the upper cuff below the third D-ring. The rearward ends of the lateral and medial portions of the upper cuff are joined together.

A first tension system connects the upper end of the lateral portion of the lower body to the lower end of the lateral portion of the upper cuff. A second tension system connects the upper end of the medial portion of the lower body to the lower end of the medial portion of the upper cuff. The first tension system includes a flat flexible member having an upper end, a lower end, a forward end and a rearward end. The first flat flexible member of the first tension system has a plurality of spaced-apart openings formed therein which define a rear rib, a front rib and an intermediate rib. The intermediate rib of the first flat flexible member has a small opening formed therein. A first eyelet assembly, including an eyelet secured to a U-shaped support, is positioned outwardly of the first flat flexible member. The first tension system includes an elongated first tensioning cord having first and second ends. The first end of the first tensioning cord is secured to the U-shaped support of the first eyelet assembly. The first end of the first tensioning cord extends rearwardly from the first eyelet assembly inwardly through the small opening in the intermediate rib, thence rearwardly and around the rear rib, thence forwardly to the front rib, thence around the front rib, thence rearwardly towards the rear rib, thence around the rear rib, thence forwardly through the small opening in the intermediate rib, thence forwardly to the U-shaped support of the first eyelet assembly and being connected thereto.

The second tension system includes a second flat flexible member having an upper end, a lower end, a forward end and a rearward end. The second flat flexible member of the second tensioning system has a plurality of spaced-apart openings formed therein which define a front rib, a rear rib and an intermediate rib. The intermediate rib of the second flat flexible member has a small opening formed therein. A second eyelet assembly including an eyelet mounted on a U-shaped support, is positioned outwardly of the second flat flexible member. An elongated second tensioning cord having first and second ends is provided. The first end of the second tensioning cord extends rearwardly from the U-shaped support of the second eyelet assembly inwardly through the small opening in the intermediate rib of the second flat flexible member, thence rearwardly and around the rear rib of the second flat flexible member, thence forwardly to the front rib of the second flat flexible member, thence around the front rib of the second flat flexible member, thence rearwardly towards the third rib of the second flat flexible member, thence around the rear rib of the second flat flexible member, thence forwardly to the small opening in the intermediate rib, thence inwardly through the small opening in the intermediate rib, thence forwardly to the U-shaped support of the second eyelet assembly and being connected thereto.

One end of the shoelace is threaded through some of the eyelets of the shoe and is then threaded through the third opening of the inclined portion of the lateral portion of the lower body, thence through the second opening of said inclined portion of said lateral portion of said lower body, thence through the first opening in said inclined portion of said medial portion of said lower body, thence through said eyelet of said first eyelet assembly, thence through said fourth D-ring, thence through said first D-ring.

The other end of the shoelace is threaded through some of the eyelets of the shoe and is then threaded through the third opening of the inclined portion of the medial portion of the lower body, thence through the second opening of said inclined portion of said medial portion of said body portion, thence through said first opening in said inclined portion of said lateral portion of said lower body, thence through said eyelet of said second eyelet assembly, thence through said second D-ring, thence through said third D-ring.

The tensioning systems of this invention functionally stabilizes the ankle as it reaches the extreme ranges of motion of providing the necessary flexibility to permit the athlete or person to function normally.

It is therefore a principal object of the invention to provide an improved ankle brace which is mounted on a shoe.

A further object of the invention is to provide an ankle brace having a lateral tension system and a medial tension system to prevent the ankle from exceeding its extreme ranges of motion while providing the necessary flexibility to permit the athlete to function normally.

These and other objects will be apparent to those skilled in the art.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

DESCRIPTION OF THE PREFERRED EMBODIMENT

Figure 1:
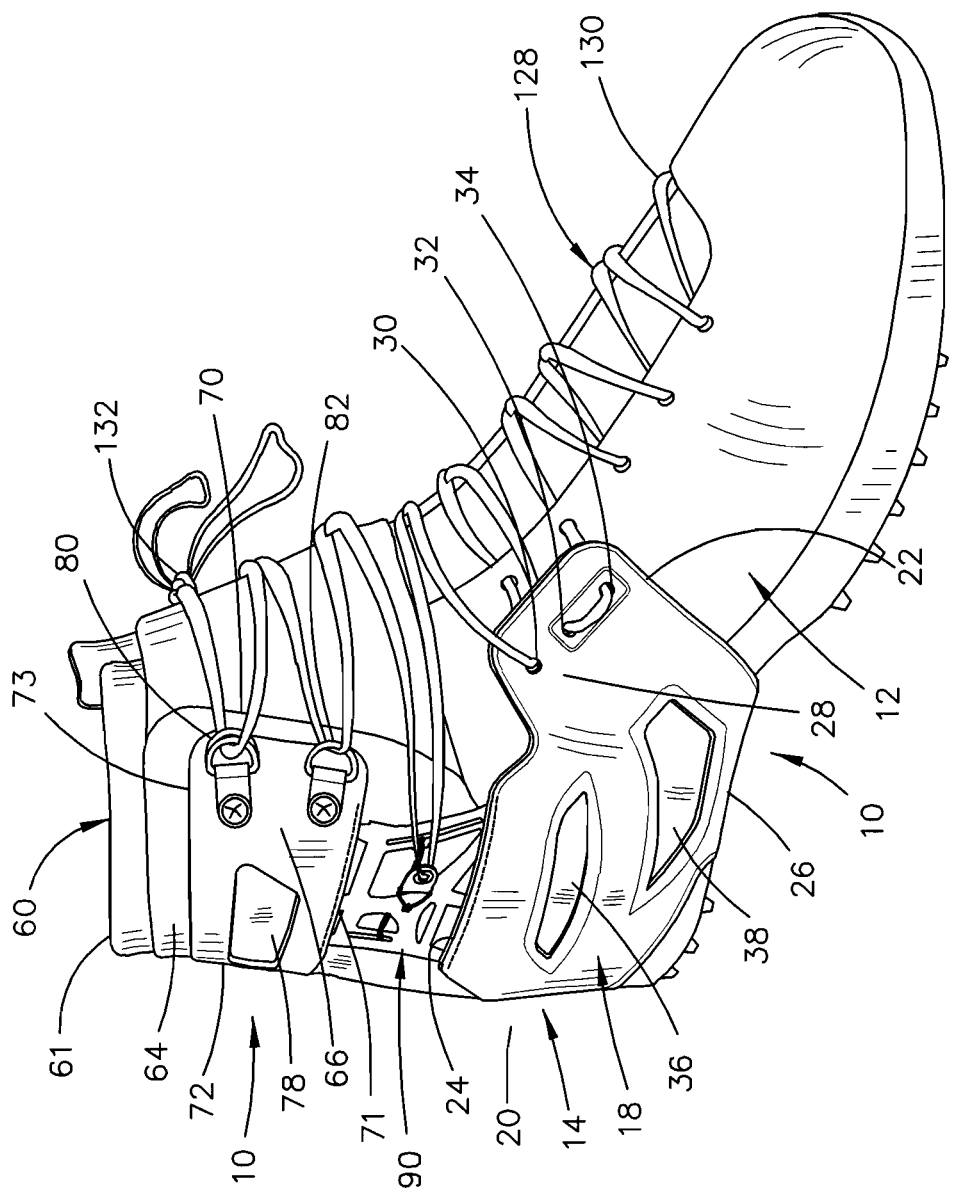
FIG. 1 is a perspective view illustrating the ankle brace of this invention mounted on an athletic shoe.
Figure 2:
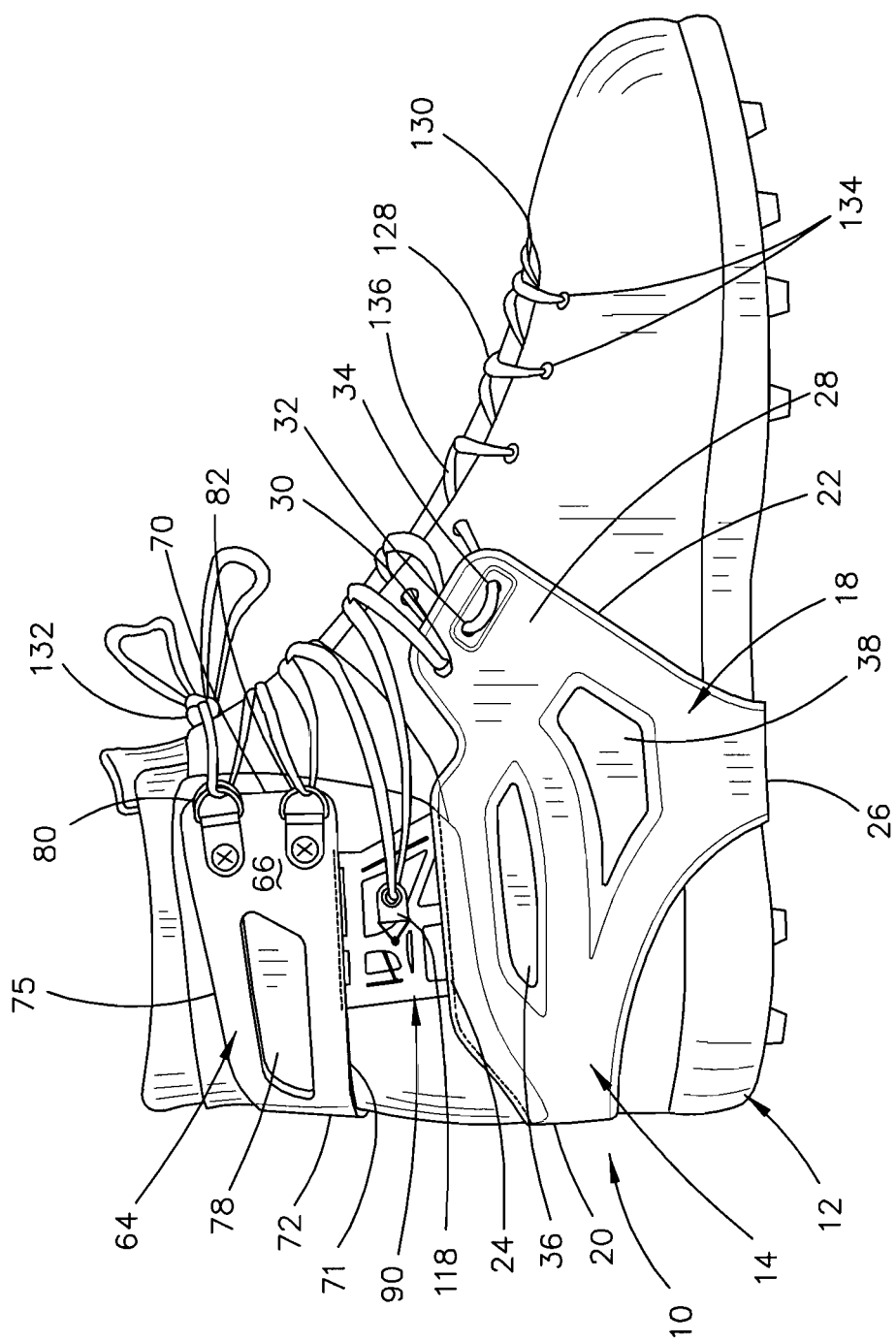
FIG. 2 is a side view of the lateral side of the ankle brace of this invention positioned on a shoe.

Embodiments are described more fully below with reference to the accompanying figures, which form a part hereof and show, by way of illustration, specific exemplary embodiments. These embodiments are disclosed in sufficient detail to enable those skilled in the art to practice the invention. However, embodiments may be implemented in many different forms and should not be construed as being limited to the embodiments set forth herein. The following detailed description is, therefore, not to be taken in a limiting sense in that the scope of the present invention is defined only by the appended claims.

The numeral 10 refers to the ankle brace of this invention which will be worn on the right foot and ankle of the wearer outside of an athletic shoe 12. Shoe 12 will be described in detail hereinafter. Ankle brace 10 will be described as having a flexible lateral portion 14 and a flexible medial portion 16. If the ankle brace 10 is worn on the left foot and ankle of the wearer, the lateral side will become the medial side and the medial side will become the lateral side. The lateral portion 14 and the medial portion 16 form a lower body 18. Preferably, lower body portion 18 is comprised of 90A TPU (frosted).

The lateral portion 14 of lower body portion 18 includes a rearward end 20, an inclined forward end 22, an upper end 24 and a lower end 26. The lateral portion 14 of lower body portion 18 includes an inclined portion 28 at its upper forward end. Inclined portion 28 includes a first opening 30, a second opening 32, and a third opening 34 formed therein. The lateral portion 14 has a pair of large openings 36 and 38 formed therein.

Figure 6:
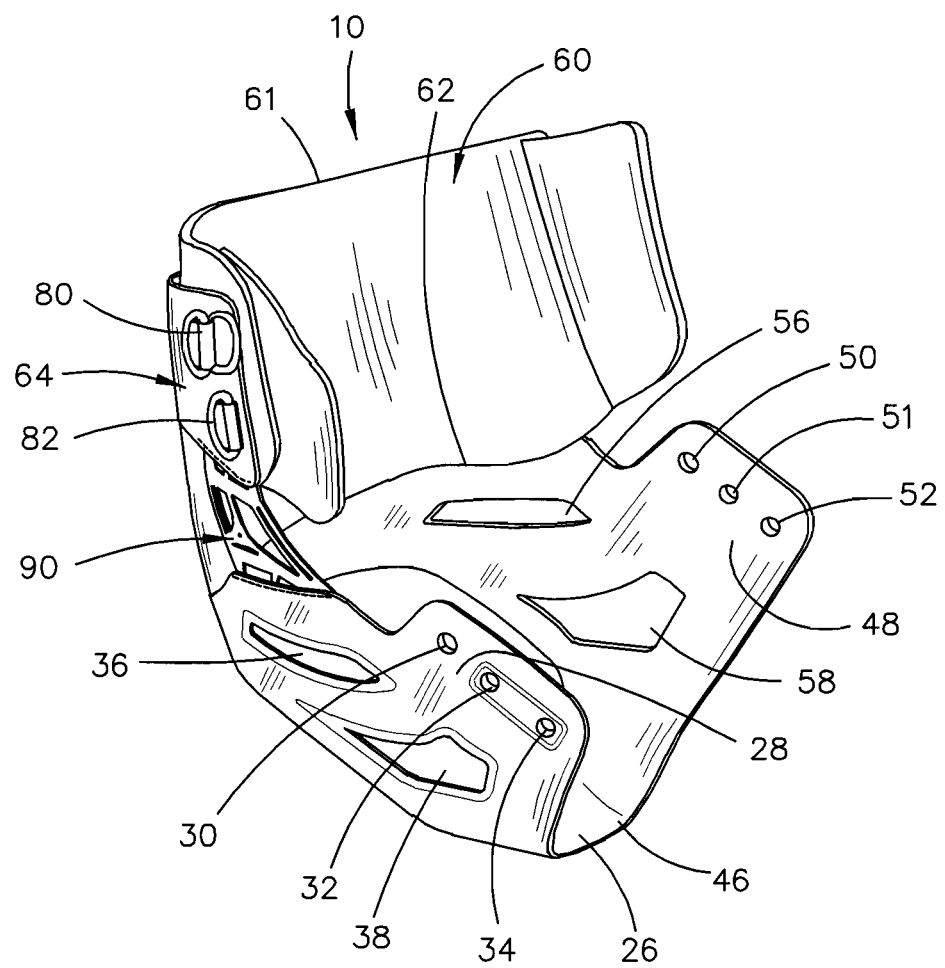
FIG. 6 is a perspective view of the ankle brace of this invention.
Figure 7:
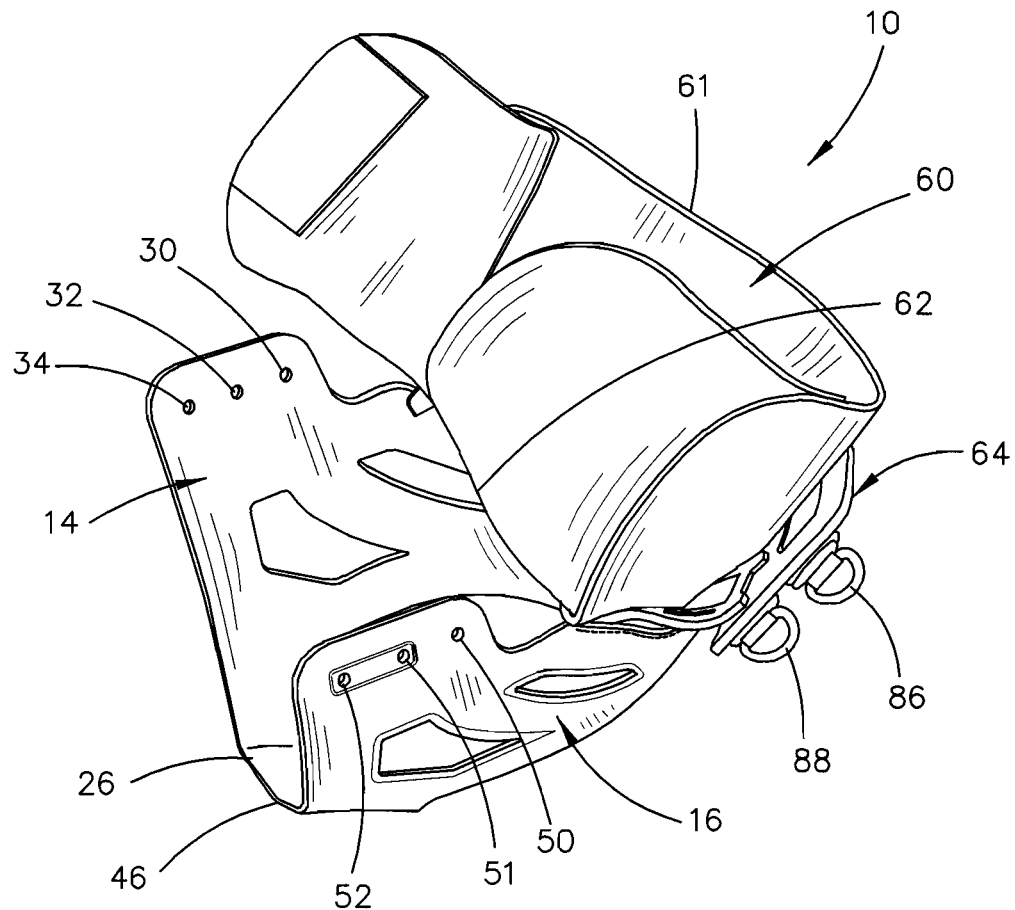
FIG. 7 is another perspective view of the ankle brace of this invention.

Medial portion 16 includes a rearward end 40, an inclined forward end 42, an upper end 44 and a lower end 46. Medial portion 16 also includes inclined portion 48 at its upper forward end. Inclined portion 48 includes a first opening 50, a second opening 51 and a third opening 52 formed therein. Medial portion 16 also includes a pair of large openings 56 and 58 formed therein. The rearward end 20 of the lateral portion 14 of lower body 18 is joined to the rearward end 40 of the medial portion 16 of lower body 18. The lower end 26 of the lateral portion 14 of the lower body 18 is joined to the lower end 46 of the medial portion 16 of lower body 18 so as to extend beneath the shoe 12 of the wearer in a U-shape as seen in FIGS. 6 and 7. The numeral 60 refers to a flexible neoprene insert which includes an upper end 61 and a lower end 62 (not shown).

The numeral 64 refers to a flexible U-shaped upper cuff having a lateral portion 66 and a medial portion 68. Lateral portion 66 has a forward end 70, a lower end 71, a rearward end 72 and an upper end 73. Medial portion 68 has a forward end 74, a lower end 75, a rearward end 76 and an upper end 77. The rearward end 72 of lateral portion 66 is joined to the rearward end 76 of medial portion 68. Thus, upper cuff 64 is of one-piece construction. Preferably, upper cuff 64 is comprised of 90 TPU (frosted).

Figure 3:
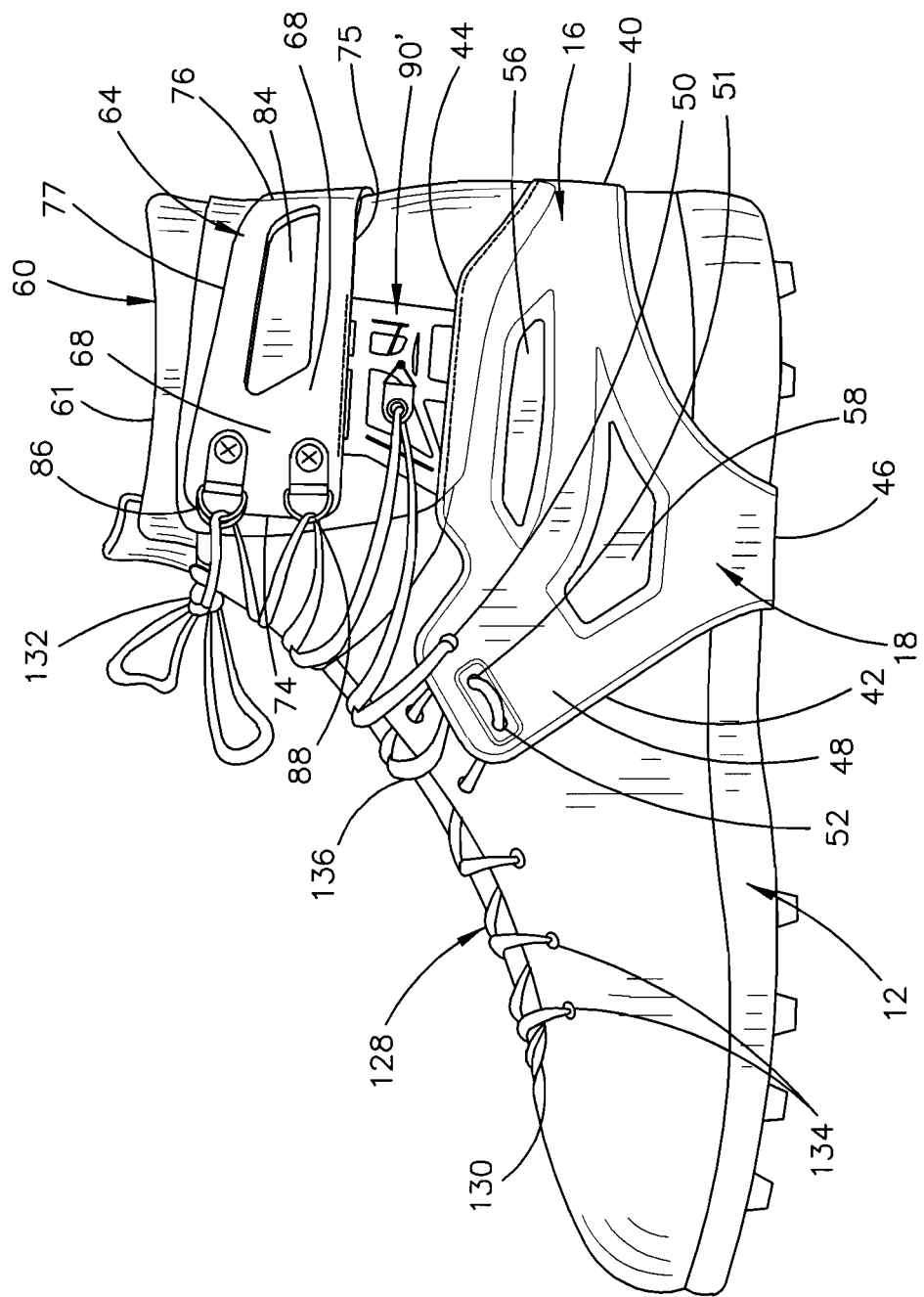
FIG. 3 is a side view of the medial side of the ankle brace of this invention positioned on a shoe.
Figure 4:
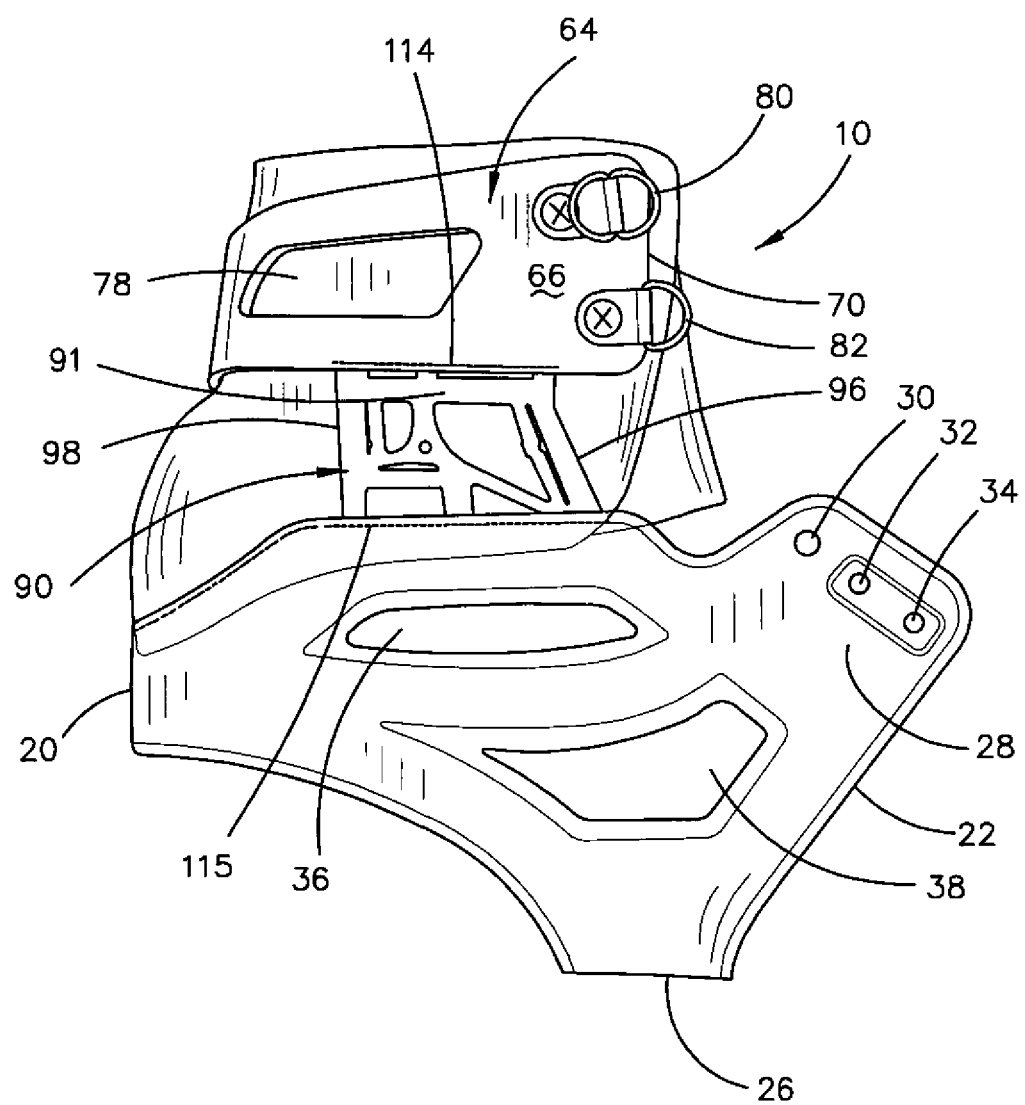
FIG. 4 is an elevational view of the lateral side of the ankle brace of this invention.
Figure 4A:
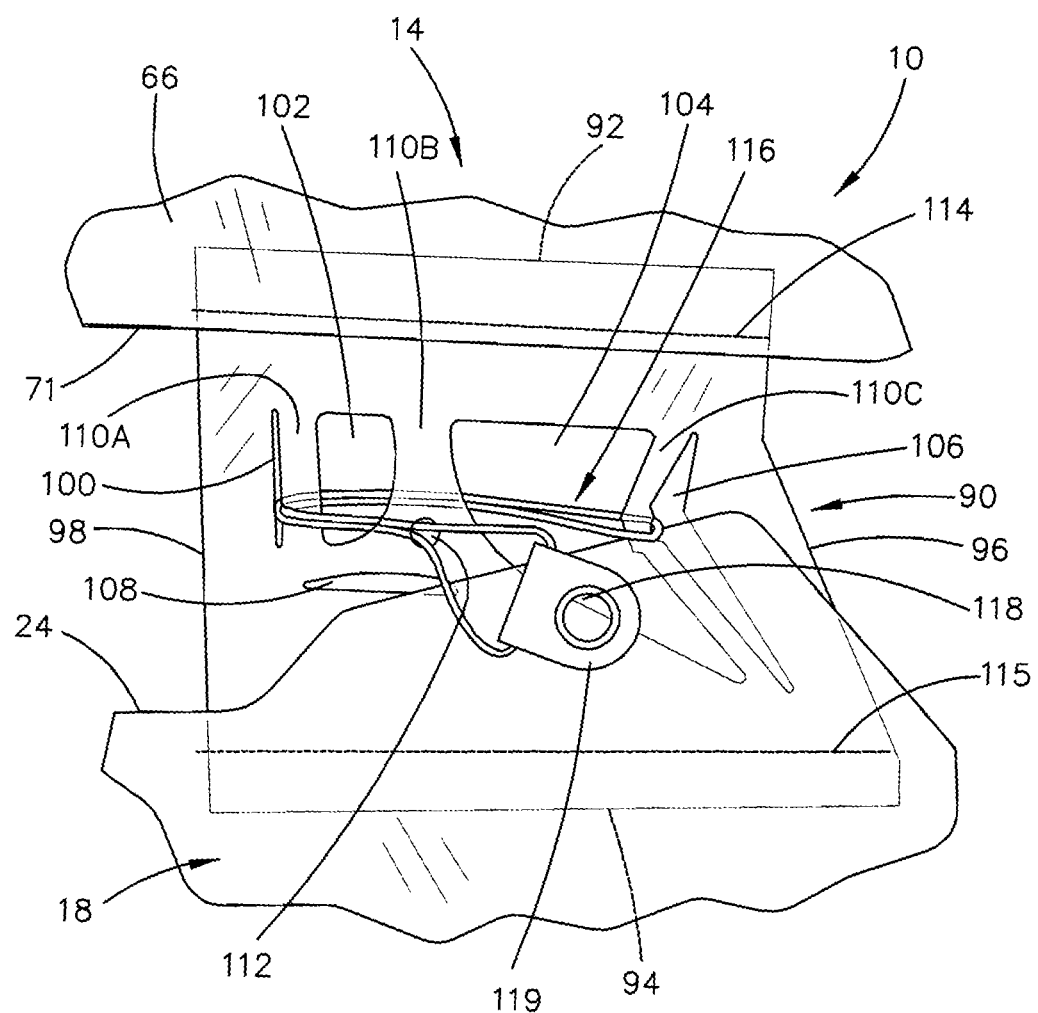
FIG. 4A is a partial elevational view of the lateral tension system.
Figure 5:
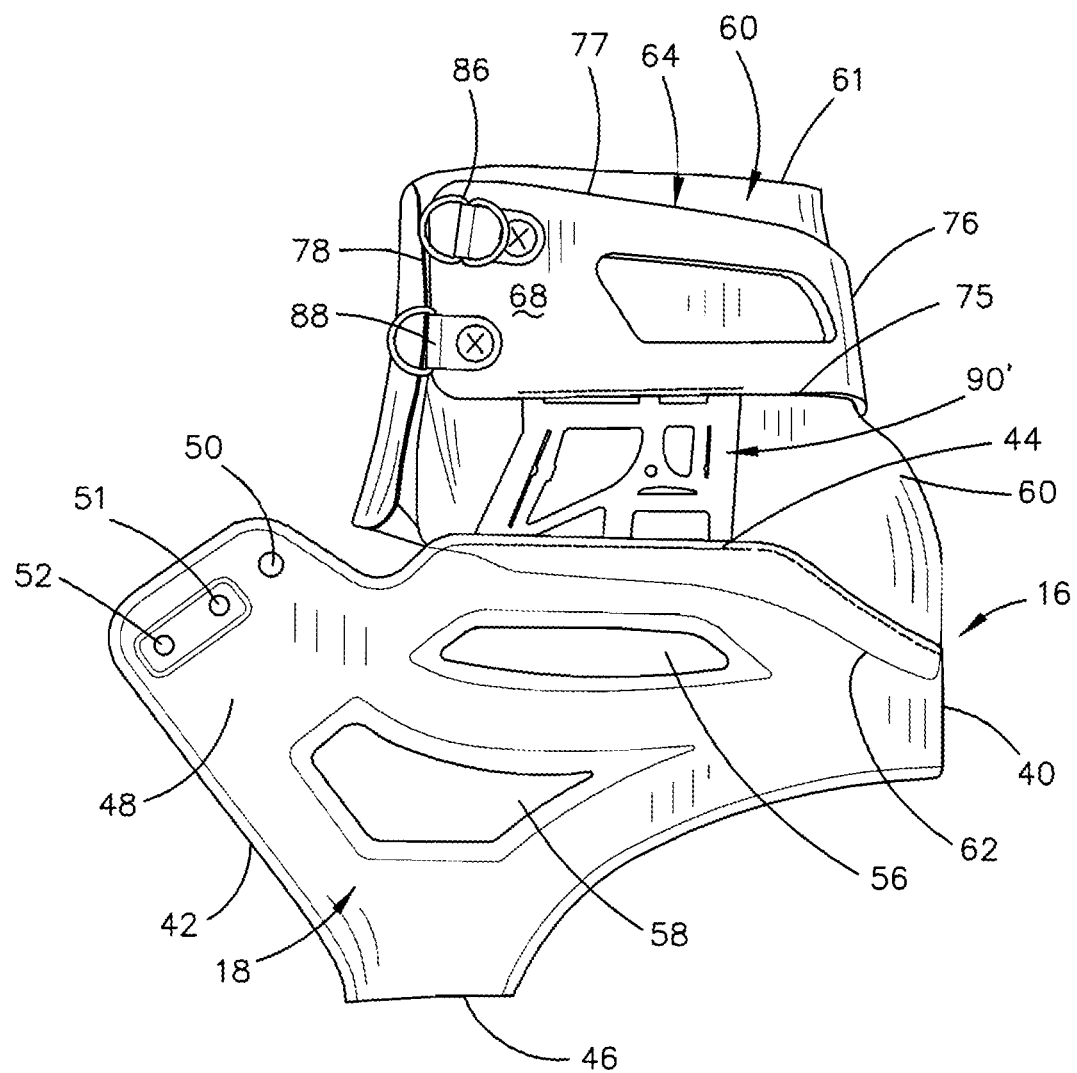
FIG. 5 is a side view of the medial side of the ankle brace of this invention.
Figure 5A:
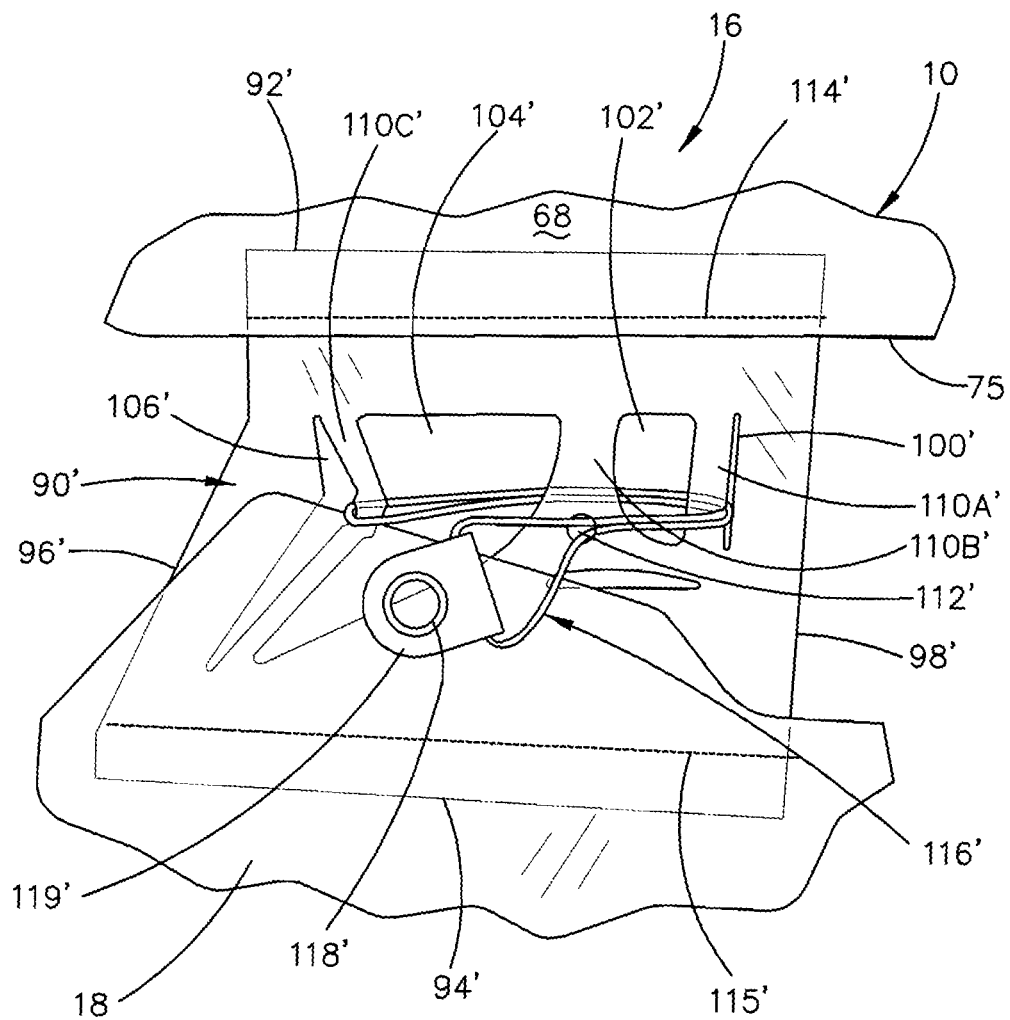
FIG. 5A is a partial elevational view of the medial tension system.

Lateral portion 66 has a large opening 78 formed therein. A double D-ring 80 is pivotally secured to lateral portion 66 of upper cuff 64 as seen in FIGS. 1 and 3. A single D-ring 82 is secured to the lateral portion 66 below the double D-ring 80. Medial portion 68 has a large opening 84 formed therein. A double D-ring 86 is pivotally secured to medial portion 68 of upper cuff 64 at the upper forward end thereof as seen in FIG. 4. A single D-ring 88 is pivotally secured to medial portion 68 of upper cuff 64 below the double D-ring 86. The upper rearward end of insert 60 is secured to the rearward end 72 of lateral portion 66 and to the rearward end 76 of medial portion 68 by stitching 89 or the like.

The numeral 90 refers to a tension system which is positioned at the lateral side of the ankle brace 16. Tension system 90 is comprised of 75A TPU (frosted) and has an upper end 92, a lower end 94, a forward end 96 and a rearward end 98. Tension system 90 includes a vertical slit or opening 100 at its rearward end. Tension system 90 includes a flat flexible member 91 and also includes horizontally spaced-apart openings including a plurality of openings 102, 104, 106 and 108 formed therein which creates a plurality of bars or ribs, such as spaced-apart ribs: 110A (rear rib), 110B (intermediate rib), and 110C (front rib) therebetween. Tension system 90 also includes a small opening 112 formed therein. The upper end 92 of tension system 90 is positioned inwardly of the lower end 71 of lateral portion 66 of upper cuff 64 and is secured thereto by stitching 114. The lower end of tension system 90 is positioned at the inner side of lateral portion 14 and is secured thereto by stitching 115. The numeral 116 refers to an elongated tensioning cord 116. The numeral 118 refers to an eyelet which is secured to a U-shaped support 119.

One end of tensioning cord 116 is extended rearwardly and inwardly from support 119 through opening 112, thence rearwardly towards slit 100, and then inwardly through slit 100, thence forwardly and inwardly of rib 110A, thence forwardly and inwardly of rib 110B, thence around rib 1100, thence rearwardly towards slit 100, thence outwardly through slit 100, thence forwardly and inwardly of rib 110B and thence outwardly through opening 112, and thence to support 119 where the ends of the tensioning cord 116 are tied together. It should be noted that the ends of the tensioning cord 116 could be tied together at other locations.

The medial portion 16 of the ankle brace 10 has a tension system 90' positioned therein which is identical to tension system 90 of lateral portion 14. Since the tension system 90' is identical to the tension system 90, it will not be described in detail. Identical structure of tension system 90' will be indicated with "'".

As stated above, ankle brace 10 is designed to be positioned outwardly of athletic shoe or non-athletic shoe 12. Shoe 12 includes a sole 120 with an underside 122 and an upper part 124. A plurality of cleats 126 extend downwardly form the underside 122 of sole 120. Upper part 124 has a lacing closure structure 128 having a lower end 130 and an upper end 132. Lacing closure structure 128 has a plurality of eyelets, grommets or lace openings 134 designed to receive a shoelace 136 in conventional fashion.

One end of the shoelace 136 is threaded through some of the eyelets 134 of the shoe 12 in conventional fashion and then threaded to the ankle brace 10 as follows:
(1) the one end of shoelace 136 is extended through the opening 34 of the inclined portion 28 of lateral portion 14 from the inner side of opening 34;
(2) the one end of shoelace 136 is extended through opening 32 of inclined portion 28 of lateral portion 14;
(3) the one end of shoelace 136 is then extended through the opening 50 in inclined portion 48 of medial portion 16 from the inner side of opening 50;
(4) the one end of shoelace 136 is then extended through eyelet 118 of lateral side 14 from the inner side of eyelet 118;
(5) the one end of shoelace 136 is then extended through D-ring 88 of medial side 16 from the inner side of D-ring 88;
(6) the one end of shoelace 136 is then extended through the double D-ring 80 of lateral side 14 from the inner side of double D-ring 80;

The other end of the shoelace 136 is threaded through some of the eyelets 134 of shoe 12 in conventional fashion and then threaded to the ankle brace 10 as follows:
(1) the other end of shoelace 136 is extended through the opening 52 of the inclined portion 48 of medial portion 16 from the inner side of opening 52;
(2) the other end of shoelace 136 is then extended through opening 51 in inclined portion 48;
(3) the other end of shoelace 136 is then extended through the opening 30 of inclined portion 28 of lateral side 14 from the inner side of opening 30;
(4) the other end of shoelace 136 is then extended through eyelet 118' of medial portion 16 from the inner side of eyelet 118';
(5) the other end of shoelace 136 is then extended through D-ring 82 of lateral side 14;
(6) the other end of shoelace 136 is then extended through the double D-ring 86 of medial portion 16 from the inner side of the double D-ring 86.

Proper tension of the ankle brace 10 is achieved by pulling on the ends of the shoelace 136 until the desired tension is achieved with the ends of the shoelaces being tied together.

The tensioning systems 90 and 90' prevent the ankle from exceeding its extreme ranges of motion while providing the necessary flexibility to permit the athlete or person to function normally.

Thus it can be seen that the invention accomplishes at least all of its stated objectives.

Although the invention has been described in language that is specific to certain structures and methodological steps, it is to be understood that the invention defined in the appended claims is not necessarily limited to the specific structures and/or steps described. Rather, the specific aspects and steps are described as forms of implementing the claimed invention. Since many embodiments of the invention can be practiced without departing from the spirit and scope of the invention, the invention resides in the claims hereinafter appended.

I claim:

1. An ankle brace for use on the outer side of a shoe having a lateral side, a medial side, an upper part with an upper end, a lacing closure, with upper and lower ends, with the lacing closure including a plurality of spaced-apart pairs of eyelets configured to have a shoelace threaded therein, comprising:
   a flexible lower body including a flexible lateral portion and a flexible medial portion;
   said lateral portion having an upper end, a lower end, a forward end, a rearward end, an outer side and an inner side;
   said lateral portion having an inclined portion, having upper and lower ends, extending upwardly and forwardly from said forward end of said lateral portion;
   said inclined portion of said lateral portion having first, second and third openings formed therein at the upper end thereof;
   said medial portion having an upper end, a lower end, a rearward end, an outer side and an inner side;
   said lower ends of said lateral and medial portions being joined together so as to pass beneath the shoe;
   said medial portion having an inclined portion, having upper and lower ends, extending upwardly and forwardly from said forward end of said medial portion;
   said inclined portion of said medial portion having first, second and third openings formed therein at said upper end thereof;
   said rearward ends of said lateral and medial portions being joined together;
   said lateral and medial portions having inner and outer sides;
   an U-shaped upper cuff having a lateral portion and a medial portion;
   said lateral portion of said upper cuff having a forward end, a rearward end, an upper end and a lower end;

said medial portion of said upper cuff having a forward end, a rearward end, an upper end and a lower end;
said lateral and medial portions of said upper cuff having inner and outer sides;
a first D-ring secured to said outer side of said lateral portion of said upper cuff at said forward end thereof;
a second D-ring secured to said outer side of said lateral portion of said upper cuff below said first D-ring;
a third D-ring secured to said outer side of said medial portion of said upper cuff at said forward end thereof;
a fourth D-ring secured to said outer side of said medial portion of said upper cuff below said third D-ring;
said rearward ends of said lateral and medial portions of said upper cuff being joined together;
a first tension system connecting said upper end of said lateral portion to said lower end of said lateral portion of said upper cuff;
a second tension system connecting said upper end of said medial portion to said lower end of said medial portion of said upper cuff;
said first tension system including a first flat flexible member having an upper end, a lower end, a forward end and a rearward end;
said first flat flexible member of said first tension system having a plurality of horizontally spaced-apart openings formed therein which define a rear rib, a front rib and an intermediate rib;
said intermediate rib of said first flat flexible member having a small opening formed therein;
a first eyelet assembly positioned outwardly of said first flat flexible member;
an elongated first tensioning cord having first and second ends;
said first end of said first tensioning cord being secured to said first eyelet assembly;
said first end of said first tensioning cord extending rearwardly from said first eyelet assembly inwardly through said small opening in said intermediate rib, thence rearwardly and around said rear rib, thence forwardly to said front rib, thence around said front rib, thence rearwardly to said rear rib, thence around said rear rib, thence forwardly towards said small opening in said intermediate rib, thence outwardly through said small opening in said intermediate rib, thence to said first eyelet assembly and being connected thereto;
said second tension system including a second flat flexible member having an upper end, a lower end, a forward end and a rearward end;
said second flat flexible member of said second tension system having a plurality of spaced-apart openings formed therein which define a front rib, a rear rib and an intermediate rib;
said intermediate rib of said second flat flexible member having a small opening formed therein;
a second eyelet assembly positioned outwardly of said second flat flexible member;
an elongated second tensioning cord having first and second ends;
said first end of said second tensioning cord being secured to said second eyelet assembly;
said first end of said second tensioning cord extending rearwardly from said second eyelet assembly inwardly through said small opening in said intermediate rib of said second flat flexible member, thence rearwardly and around said rear rib of said second flat flexible member, thence forwardly to said front rib of said second flat flexible member, thence around said front rib of said second flat flexible member, thence rearwardly towards said rear rib of said second flat flexible member, thence around said rear rib of said second flat flexible member, thence forwardly to said small opening in said intermediate rib, thence inwardly through said small opening in said intermediate rib, thence forwardly to said second eyelet assembly and being connected thereto;
one end of the shoelace being threaded through some of the eyelets of the shoe and then being threaded through said first opening in said inclined portion of said lateral portion, through said second opening in said inclined portion of said lateral portion, through said third opening of said inclined portion of said medial portion, thence through said first eyelet assembly, thence through said fourth D-ring, and thence through said first D-ring;
the other end of the shoelace being threaded through some of the eyelets of the shoe and then being threaded through said first opening in said inclined portion of said medial portion, through said second opening in said inclined portion of said medial portion, thence through said third opening of said inclined portion of said lateral portion, thence through said second eyelet assembly, thence through said third D-ring, thence through said first D-ring; and
said one end of said shoelace and said other end of said shoelace being tied together.

2. The ankle brace of claim 1 wherein said first and third D-rings are double D-rings.

3. The ankle brace of claim 1 wherein said shoe is an athletic shoe.

4. An ankle brace for use on a shoe having a lateral side, a medial side, an upper part with an upper end, a lacing closure, with upper and lower ends, with the lacing closure including a plurality of spaced-apart pairs of eyelets configured to have a shoelace threaded therein, comprising:
a lower body including a flexible lateral portion and a flexible medial portion;
said lateral portion having an upper end, a lower end, a forward end, a rearward end, an outer side and an inner side;
said forward end of said lateral portion having at least first and second openings formed therein;
said medial portion having an upper end, a lower end, a rearward end, an outer side and an inner side;
said forward end of said medial portion having at least first and second openings formed therein;
said rearward ends of said lateral and medial portions being joined together;
said lower ends of said lateral and medial portions being joined together so as to pass beneath the shoe;
an U-shaped upper cuff having a lateral portion and a medial portion;
said lateral portion of said upper cuff having a forward end, a rearward end, an upper end and a lower end;
said medial portion of said upper cuff having a forward end, a rearward end, an upper end and a lower end;
a first D-ring secured to said outer side of said lateral portion of said upper cuff at said forward end thereof;
a second D-ring secured to said outer side of said lateral portion of said upper cuff below said first D-ring;
a third D-ring secured to said outer side of said medial portion of said upper cuff at said forward end thereof;
a fourth D-ring secured to said outer side of said medial portion of said upper cuff below said third D-ring;
said rearward ends of said lateral and medial portions of said upper cuff being joined together;

a first tension system connecting said upper end of said lateral portion to said lower end of lateral portion of said upper cuff;

a second tension system connecting said upper end of said medial portion to said lower end of said medial portion of said upper cuff;

said first tension system including a first flat flexible member having an upper end, a lower end, a forward end and a rearward end;

said first flat flexible member of said first tension system having a plurality of spaced-apart openings formed therein which define a plurality of spaced-apart ribs;

one of said ribs of said first flat flexible member having a small opening formed therein;

a first eyelet assembly positioned outwardly of said first flat flexible member;

an elongated first tensioning cord having first and second ends;

said first end of said first tensioning cord being secured to said first eyelet assembly;

said first end of said first tensioning cord extending rearwardly from said first eyelet assembly towards said small opening, through said small opening, thence to a first rib positioned rearwardly of said small opening, thence around the first rib, thence forwardly to a second rib which is positioned forwardly of said small opening, thence around said second rib, thence rearwardly towards said first rib, thence around said first rib, thence forwardly towards said small opening, thence through said small opening, thence rearwardly to said first eyelet assembly and being connected thereto;

said second tension system including a second flat flexible member having an upper end, a lower end, a forward end and a rearward end;

said second flat flexible member of said second tension system having a plurality of spaced-apart openings formed therein which define a plurality of ribs;

one of said ribs of said second flat flexible member having a small opening formed therein;

a second eyelet assembly positioned outwardly of said second flat flexible member;

an elongated second tensioning cord having first and second ends;

said first end of said second tensioning cord being secured to said second eyelet assembly;

said end of said second tensioning cord extending rearwardly from said second eyelet assembly towards said small opening, thence through said small opening, thence rearwardly to a first rib, thence around said first rib, thence forwardly to a second rib which is positioned forwardly of said second eyelet assembly, thence rearwardly to said first rib, thence around said first rib, thence forwardly to said small opening, thence through said small opening, thence forwardly to said second eyelet assembly and being operatively connected thereto;

one end of the shoelace being threaded through some of the eyelets of the shoe and then being threaded through said first opening in said lateral portion, thence through said second opening of said medial portion, thence through said first eyelet assembly, thence through said fourth D-ring, and thence through said first D-ring;

the other end of the shoelace being threaded through some of the eyelets of the shoe and then being threaded through said first opening in said medial portion, thence through said second opening of said lateral portion, thence through said second eyelet assembly, thence through said third D-ring, thence through said first D-ring; and said one end of said shoelace and said other end of said shoelace being tied together.

5. The ankle brace of claim 4 wherein said first and third D-rings are Double D-rings.

* * * * *